US00PP10644P

United States Patent [19]

Brits

[11] Patent Number: Plant 10,644

[45] Date of Patent: Oct. 13, 1998

[54] LEUCOSPERMUM PLANT NAMED 'HIGH GOLD'

[75] Inventor: Gert Johannes Brits, Elsenburg, South Africa

[73] Assignee: Zorro Protea Farms, Escondido, Calif.

[21] Appl. No.: 887,982

[22] Filed: Jul. 3, 1997

[51] Int. Cl.[6] ..... A01H 5/00

[52] U.S. Cl. ..... Plt./54.1

[58] Field of Search ..... Plt./68.1, 54.1

[56] References Cited

PUBLICATIONS

GTITM UPOVROM Citation for 'High Gold' as per AU PBR 94206; Oct. 17, 1994.

*Primary Examiner*—Howard J. Locker
*Assistant Examiner*—Kent L. Bell
*Attorney, Agent, or Firm*—C. A. Whealy

[57] ABSTRACT

A distinct cultivar of Leucospermum plant named 'High Gold', characterized by its large bright yellow inflorescences that are about 8.5 cm in diameter; numerous, long, straight flowering stems; inflorescences positioned perpendicular to the flowering stem; good vigor; attractive dark green foliage; early flowering; and excellent postproduction longevity.

1 Drawing Sheet

The present invention relates to a new and distinct cultivar of Leucospermum plant, botanically known as *Leucospermum cordifolium*×*Leucospermum patersonii* and referred to by the cultivar name 'High Gold'.

The new cultivar is a product of a planned breeding program conducted by the inventor in Riviersonderend, South Africa. The objective of the breeding program is to create new Leucospermum cultivars having inflorescences with desirable colors, straight stems, good form and vigor.

The new cultivar originated from a cross made by the inventor in Riviersonderend, South Africa, of the nonpatented *Leucospermum cordifolium* cultivar 'Yellow Bird' as the female parent with the species *Leucospermum patersonii* as the male parent. The cultivar 'High Gold' was discovered and selected by the inventor as a flowering plant within the progeny of the stated cross in a controlled environment in Riviersonderend, South Africa in 1984. The selection of this plant was based on its desirable inflorescence color, straight flower stems, good vigor and excellent postproduction longevity.

Asexual reproduction of the new cultivar by terminal cuttings taken in a controlled environment in Riviersonderend, South Africa, has shown that the unique features of this new Leucospermum are stable and reproduced true to type in successive generations.

The cultivar 'High Gold' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'High Gold'. These characteristics in combination distinguish 'High Gold' as a new and distinct cultivar:

1. Large bright yellow inflorescences that are about 8.5 cm in diameter.
2. Numerous, long, straight flowering stems.
3. Inflorescences positioned perpendicular to the flowering stem.
4. Good vigor.
5. Attractive dark green foliage.
6. Early flowering.
7. Excellent postproduction longevity with inflorescences maintaining yellow inflorescence color for three to four weeks in an interior environment.

Plants of the new cultivar resemble plants of the female parent, the *Leucospermum cordifolium* cultivar 'Yellow Bird', in inflorescence color and size, however they differ in the following characteristics:

1. Plants of the new cultivar are more vigorous than plants of the cultivar 'Yellow Bird'.
2. Plants of the new cultivar have broader leaves than plants of the cultivar 'Yellow Bird'.
3. Plants of the new cultivar have longer, thicker, stronger and straighter stems than plants of the cultivar 'Yellow Bird'. Plants of the cultivar 'Yellow Bird' tend to grow horizontally with the inflorescences at right angles to the stems whereas plants of the new cultivar grow upright with inflorescences positioned perpendicular to the stems. Because of the position of the inflorescences, flowering stems of the cultivar 'Yellow Bird' are not as desirable as flowering stems of the new cultivar for floral arrangements and are more easily damaged during shipment.
4. Plants of the new cultivar have inflorescences that are spherical in shape whereas plants of the cultivar 'Yellow Gold' have inflorescences that are squattier, shorter and flattened at the base.
5. Plants of the new cultivar have more flowers per inflorescence than plants of the cultivar 'Yellow Bird'.
6. Plants of the new cultivar usually flower about two to three weeks earlier than plants of the cultivar 'Yellow Bird'.
7. Cut flowers of the new cultivar have greater postproduction longevity than cut flowers of the cultivar 'Yellow Bird'.

Plants of the new cultivar resemble plants of the male parent, the species *Leucospermum patersonii,* in inflorescence shape and orientation, however they differ in the following characteristics:

1. Plants of the new cultivar have longer stems than plants of *Leucospermum patersonii.*
2. Plants of the new cultivar have smaller and darker green leaves than plants of *Leucospermum patersonii.* Additionally, leaves of the new cultivar are cordate in shape with dentate to acute apices whereas leaves of *Leucospermum patersonii* are elliptic in shape with a characteristic five-dentate apices.
3. Plants of the new cultivar have larger and more dense inflorescences than plants of *Leucospermum patersonii.*
4. Flowers are yellow in color on plants of the new cultivar whereas flowers of *Leucospermum patersonii* are orange.

5. Plants of the new cultivar have almost twice as many flowers as plants of *Leucospermum patersonii.*

6. Cut flowers of the new cultivar have greater postproduction longevity than cut flowers of *Leucospermum patersonii.*

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical flowering plant of 'High Gold'. Flower and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in San Diego, Calif. under commercial field practice. Plants were produced in full sunlight with day temperatures ranging from 13° to 35° C. and night temperatures ranging from 0° to 18° C.

Botanical classification: *Leucospermum cordifolium*× *Leucospermum patersonii* cultivar 'High Gold'.

Commercial classification: Cut flower Leucospermum.

Parentage:

*Female or seed parent.*—*Leucospermum cordifolium* cultivar 'Yellow Bird', not patented.

*Male or pollen parent.*—Species *Leucospermum patersonii.*

Propagation:

*Type.*—Cuttings.

*Time to initiate roots.*—About eight weeks, soil temperatures of 22° C.

*Time to develop roots.*—About 10 weeks, soil temperatures of 22° C.

*Rooting habit.*—Fine.

Plant description:

*Appearance.*—Perennial woody shrub used as a cut flower. Stems upright, freely branching, inflorescences perpendicular to flower stem. Numerous flowering stems per plant, vigorous.

*Flowering stem.*—Appearance: Upright, very straight, strong and thick. Length: About 100 cm. Diameter: About 1.25 cm. Internode length: About 1.5 cm. Texture: Very fine pubescence. Color: 144B.

*Foliage description.*—Leaf arrangement: Alternate, single, sessile. Leaf size, fully expanded: Length: About 4 cm. Width: About 3 cm. Leaf apex: Initially dentate, becoming acute. Leaf base: Cordate. Leaf margin: Entire. Leaf texture: Leathery, tough, thick and glabrous. Color: Young foliage adaxial surface: 147A or slightly lighter. Young foliage abaxial surface: 147A. Mature foliage abaxial surface: 147A. Mature foliage adaxial surface: 147A. Venation abaxial surface: 147B. Venation adaxial surface: 147B.

Flowering description: With the exception of inflorescence color, shape and size, flowers are typical of the species Leucospermum.

*Appearance.*—Inflorescences spherical and borne single on terminals perpendicular to the flower stem. Numerous flowers arranged spirally on a conical capitulum.

*Postproduction longevity.*—In an interior environment, flowering stems will maintain good color and substance for three or four weeks.

*Inflorescence size.*—Diameter: About 8.5 cm. Depth (height): About 8.5 cm. Diameter of capitulum: About 1.5 cm. Depth (height) of capitulum: About 6 cm. Quantity of flowers per inflorescence: About 270.

*Bracts.*—Shape: Elongated, broad at base and sharply pointed at apex. Margin: Entire. Texture: Very heavily whiskered. Number of bracts per inflorescence: About 270. Color: 144A.

*Stamens.*—Quantity: Four per flower, surrounding style. Length: About 2 cm. Texture: Heavily whiskered at base. Color: 13A at apex and mid-section, 145A at base. Anther shape: Lanceolate. Anther length: About 2 mm. Anther width: About 1 mm. Anther color: 17A. Amount of pollen: Low to moderate. Pollen color: 17A.

*Pistils.*—Quantity: One per flower. Pistil length: About 5 cm. Style orientation: Curved upright. Style length: 4.6 cm. Style color: 13A at apex and mid-section, 145B towards base. Stigma shape: Flat and circular. Stigma color: 13A.

Disease resistance: The new Leucospermum has not exhibited any notable resistance to diseases commonly observed on species of Leucospermum.

Seed production: Seed production has not been observed on plants produced in San Diego, Calif.

It is claimed:

1. A new and distinct cultivar of Leucospermum plant named 'High Gold', as illustrated and described.

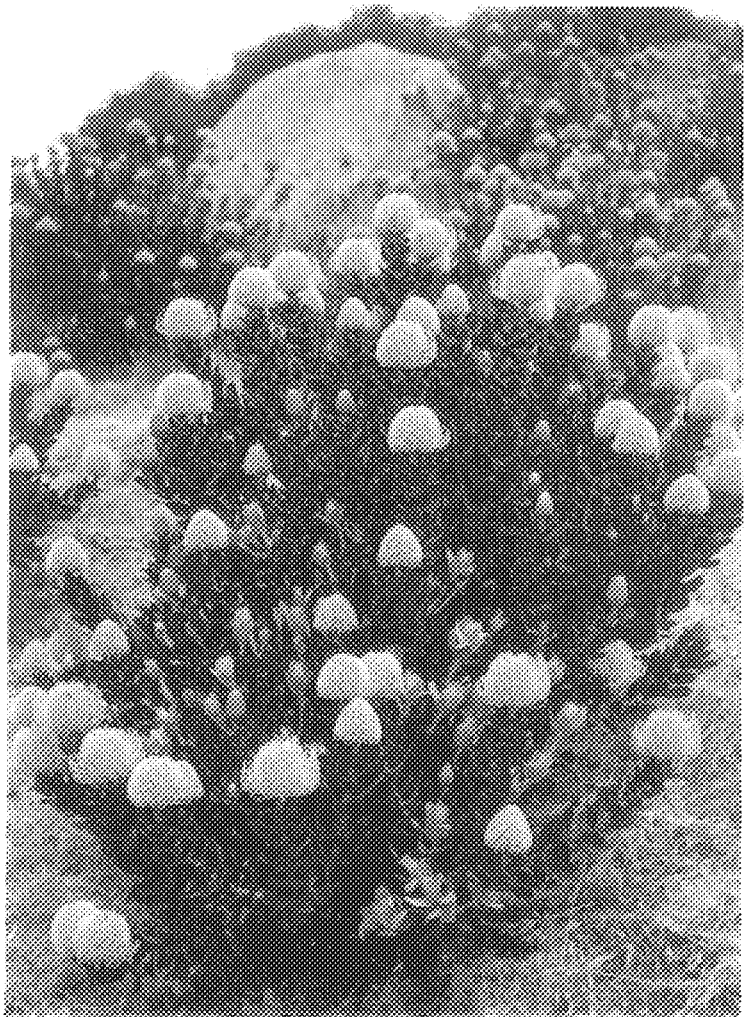

* * * * *